United States Patent [19]

Tsuchiya et al.

[11] Patent Number: 4,920,386
[45] Date of Patent: Apr. 24, 1990

[54] HIGH SPATIAL AND TIME RESOLUTION MEASURING APPARATUS

[75] Inventors: Yutaka Tsuchiya; Yoshihiro Takiguchi, both of Shizuoka, Japan

[73] Assignee: Hamamatsu Photonics Kabushiki Kaisha, Hamamatsu, Japan

[21] Appl. No.: 339,920

[22] Filed: Apr. 19, 1989

Related U.S. Application Data

[63] Continuation of Ser. No. 88,284, Aug. 24, 1987, abandoned.

[30] Foreign Application Priority Data

Aug. 25, 1986 [JP]  Japan ................................. 61-197031

[51] Int. Cl.$^5$ ..................... G01N 21/64; G01N 21/59
[52] U.S. Cl. ............................. 356/417; 250/213 VT; 356/318; 356/432
[58] Field of Search ............... 356/317, 318, 417, 432; 250/213 VT

[56] References Cited

U.S. PATENT DOCUMENTS

| | | | |
|---|---|---|---|
| 4,195,930 | 4/1980 | Delhaye et al. | 356/318 X |
| 4,327,285 | 4/1982 | Bradley | 250/213 VT |
| 4,444,317 | 4/1984 | Wick et al. | 356/318 X |
| 4,600,306 | 7/1986 | Hara et al. | 356/317 |
| 4,611,920 | 9/1986 | Tsuchiya | 250/213 VT X |
| 4,630,925 | 12/1986 | Schiller et al. | 356/318 |
| 4,662,747 | 5/1987 | Isaacson et al. | 356/317 |

Primary Examiner—Vincent P. McGraw
Attorney, Agent, or Firm—Finnegan, Henderson, Farabow, Garrett and Dunner

[57] ABSTRACT

A high spatial and time resolution measuring apparatus for optically measuring a fine area in an object to be measured, the apparatus comprising a stage for mounting a specimen thereon, a light source for generating a first light, a first optical system for leading the first light from the light source to the specimen, an objective lens for magnifying an image of a second light from the specimen, a second optical system for imaging a part of the image in a form of a slit, a streak tube having a photocathode at a position of image formation of the second optical system for receiving the part of the image and forming a streak image thereof, a housing for shielding the first optical system, the objective lens and the second optical system from stray light.

27 Claims, 3 Drawing Sheets

HIGH SPATIAL AND TIME RESOLUTION MEASURING APPARATUS

This application is a continuation of application Ser. No. 088,284, filed Aug. 24, 1987, now abandoned.

BACKGROUND OF THE INVENTION

1. Field of the Invention

The present invention relates to an apparatus for optically measuring a fine area in an object to be measured with high spatial and time resolution.

2. Prior Art

Recently, the necessity of optically measuring a fine area in an object of measurement with high spatial and time resolution has increased in the fields of biophysics, life science, chemistry, biology and the like. For example, such necessity has occurred in the case of detecting a tumor cell mixed into normal cells by using the fluorescent phenomenon of HpD incorporated into the tumor cell or in the case of measuring the HpD distribution in a tumor cell. In those case, it is necessary to measure a fine area of the order of tens of $\mu$m, so that the spatial resolution of the order of $\mu$m and the time resolution of the order of ps are required.

For such measurement, a method using a microscope and a streak camera in combination may be proposed. However, the method has problems as follows.

(1) When the microscope and the streak camera are combined, the optically adjusting or slightly adjusting mechanism becomes complicated.

(2) It is difficult to integrate the microscope and the streak camera to one body.

(3) The laser light incident on the specimen to generate fluorescent light is reflected from the surfaces or interfaces of lenses and the like constructing a complex optical system in the microscope, so that the specimen is re-excited by the reflected light (refer to FIG. 1) to thereby cause mismeasurement.

(4) From the same reason as described in the paragraph (3), the fluorescent light to be measured is reflected from the surfaces or interfaces of optical elements, so that the reflected fluorescent light with a little delay is overlapped onto the fluorescent light to be measured (refer to FIG. 2) to make it impossible to carry out the time resolution measurement of true fluorescence.

(5) Generally, a scale-down system is essential as an optical system for using the microscope and the streak camera in combination, so that not only the adjustment as described in the paragraphs (1) and (2) is more complicated but also the same problem as described in the paragraphs (3) and (4) exists in reflection in the scale-down system.

From the aforementioned problems, there is heretofore no existence of measuring apparatus capable of optically measuring a fine area in an object of measurement with very high spatial and time resolution.

SUMMARY OF THE INVENTION

It is therefore an object of the present invention to provide an apparatus capable of optically measuring a fine area with very high spatial and time resolution.

According to a first aspect of the present invention, the high spatial and time resolution measuring apparatus comprises a stage for mounting a specimen thereon; a light source for generating a first light; a first optical means for leading said first light from said light source to said specimen; an objective lens for magnifying an image of a second light from said specimen; a second optical means for imaging a part of said image in a form of a slit; a streak tube having a photocathode at a position of image formation of said second optical system for receiving said part of said image and forming a streak image thereof; a housing for shielding said first optical means, said objective lens and said second optical means from stray light.

According to a second aspect of the present invention, the high spatial and time resolution measuring apparatus further comprises, in addition to those constituent components described above according to the first aspect of the invention, a television camera for picking up a streak image on a phosphor screen of the streak tube, and a controller for controlling drive of the stage, light emission of the second optical means, a deflection voltage of the streak tube, and the television camera.

The stage used in the present invention may be slightly movable in the direction of the optical axis of the objective lens or in the direction perpendicular to the optical axis. In this case, an actuator is provided.

DETAILED DESCRIPTION OF THE INVENTION

Figure 1:
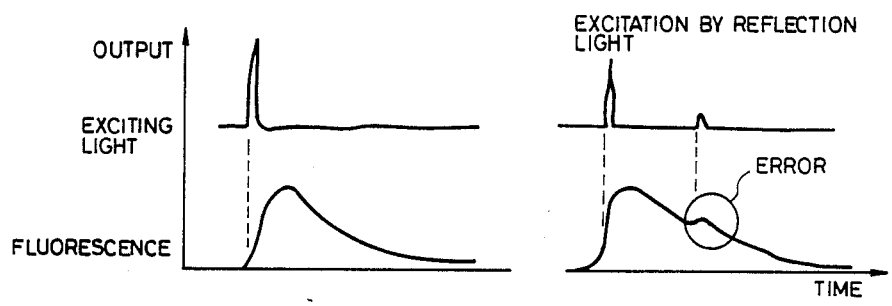
FIGS. 1 and 2 are views for explaining mismeasurement which occurs in the case where the microscope and the streak camera are used in combination.
Figure 2:
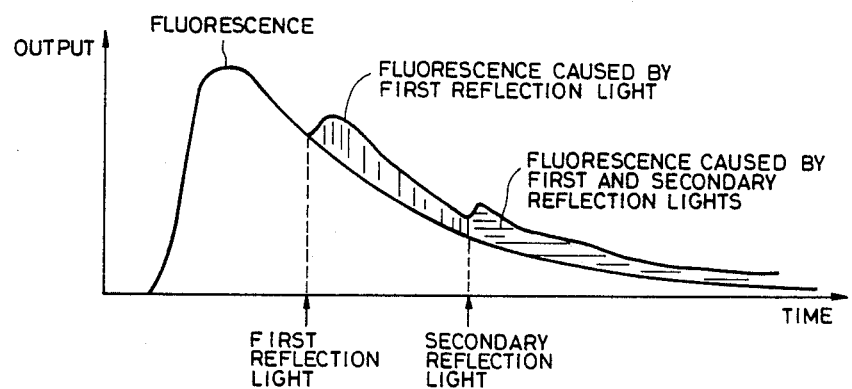

The streak camera has the spatial resolution of 20 $\mu$m or less on the photoelectric surface of the streak tube. It is therefore sufficient to use an objective lens of about 50 magnifying power at the maximum. When the objective lens has 50 magnifying power, an observing means are required for searching an object of measurement and for adjusting the focus. Therefore, the streak camera is used with a focusing mode. In other words, the streak camera is used as an image intensifier, in which the incident slit width of the streak camera is enlarged and a sweeping operation for time resolution is interrupted. Even in this case, the spatial resolution is almost the same as that in the case of the sweep mode.

The microscope has its original object for observation with the naked eye. In the case where a 50-power objective lens is used as in the apparatus of the present invention, the size of 1 $\mu$m cannot be observed as the size larger than 0.5 mm even if an eye lens having 10 magnifying power (generally used in a 5-power or a 10-power eye lens). Accordingly, in the case of microscopic observation with the naked eye, a 100-power objective lens should be used to attain the spatial resolution of 1 $\mu$m. Accordingly, in the case where the microscope and the streak camera are used in combination, it is necessary that a scale-down lens system is provided between the microscope and the streak camera.

Further, a relay lens may be disposed after the objective lens. In this case, the magnifying power of the optical system composed of the objective lens and the relay lens is about 50 at the maximum.

The lighting device may be of a downward illumination type, may be of a transillumination type, or may be of a type formed by combination of a downward illumination type and a transillumination type. The light source of the lighting device may be a white-heat lamp, an electric-discharge lamp, a laser, or a pulse light source. A semiconductor laser, a solid laser, a gas laser or a dye laser may be used as the laser. Further, a short-pulse continuous light source variable in pulse interval may be used as the light source. In this invention, a specimen is radiaated with a light from the light source as described above to observe a reflected light from the specimen, a transmitted light through the specimen or an emitted light by the specimen such as florescent light or the like which is generated in the specimen by the incidence of the light from the light source.

The objective lens may be formed of a microscopic objective lens or may be formed of a still camera lens. Further, the objective lens may be formed of a combination of these lenses.

The slit is variable in the width for example within a range of from 0 to 5 mm. The slit width is enlarged for the focusing mode (micro-observation). For time-resolved measurement, the slit width is determined within a range of from 10 $\mu$m to 50 $\mu$m.

Density filters, interference filters, polarizing filters or color filters may be respectively inserted into the relay lens and/or the illumination optical system. Further, the objective lens may be disposed so that the optical axis of the objective lens can intersect the optical axis of the streak tube at a desired arbitrary angle. Further, a reflecting mirror may be disposed at the intersection point of the two optical axes so as to be rotatable round an axis perpendicular to the two optical axes.

The deflection voltage of the streak tube is triggered by synchronization with the pulse light generated from the light source of the lighting device. The trigger voltage can be generated by a circuit constituted by a photodiode, an amplifier and a delay circuit.

Further, a television monitor may be connected to the apparatus so that a weak input image can be continuously observed at real time.

In the thus arranged apparatus, the specimen irradiated is magnified by the objective lens. The specimen image is slit and then formed on the photocathode of the streak tube. The magnified specimen image is slit to attain a part necessary for measurement. In the streak tube, the photoelectron image formed on the photocathode is locally swept for reproduction of an optical image on the phosphor screen. The image on the phosphor screen is recorded by the still camera or picked up by the television camera for display on the television monitor. The controller controls the drive of the stage, the light-emission time of the light source in the lighting device, and the delay time required for synchronization of the illumination light with the streak tube.

Further, in the case where the controller serves as a streak image processor, the controller also controls the function of the streak image processor.

Figures 3, 4:
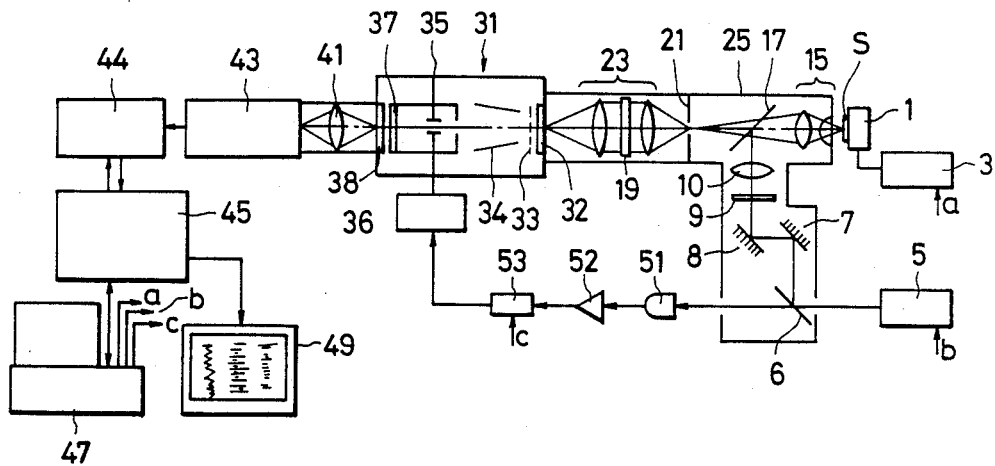
FIG. 3 is a general diagrammatic view of an apparatus as an embodiment of the present invention.
FIGS. 4 to 6 are partial diagrammatic views of illuminating and image-forming systems as other embodiments of the invention, used in the apparatus of FIG. 3.

FIG. 3 is a general diagrammatic view of an apparatus, which shows a first embodiment of the present invention.

Referring to the drawing, a stage 1 for mounting a specimen S is linked to an actuator 3. The actuator 3 is constituted by a pulse motor, a screw mechanism and the like (which are not shown). By the actuator 3, the stage 1 can be slightly moved in the direction of the optical axis of an objective lens 15 and in the direction perpendicular to that optical axis, whereby the image of the specimen can be focused on a photocathode 32 of a streak tube 31 and the range of measurement for the specimen S can be changed. A slide carrying the specimen S, cover glass put on the specimen, and the like, must be inclined relative to the optical axis so that the reflected light cannot enter the optical system for forming the image of the specimen S.

The lighting device is of a downward illumination type, in which a light source 5 is constituted by a semiconductor laser oscillator which continuously generates short-pulse laser light. The pulse interval can be changed. The laser light is split by a beam splitter 6, and then the split light is successively passed through reflecting mirrors 7 and 8, an illumination-system filter 9, an illumination lens 10, a beam splitter 17 and the objective lens 15 to thereby irradiate the surface of the specimen S. The illumination-system filter 9 can be selected from an interference filter, a color filter, a density filter, a polarizing filter and the like.

As the objective lens 15, employed is a microscopic objective lens. In this embodiment, the objective lens 15 has 40 magnifying power.

In the rear of the beam splitter 17, a width-variable slit 21 is disposed at the position of image formation of the objective lens 15. The width-variable slit 21 limits the visual field of the specimen S at measurement to thereby decide the range of measurement.

A relay lens 23 is disposed in the rear of the width-variable slit 21. A filter 19 selected from an interference filter, a polarizing filter, a color filter and the like, is inserted into the relay lens 23. The filter 19 must be slightly inclined relative to the optical axis so that the reflected light cannot enter the optical system for forming the image of the specimen S. The chromatic aberration of the relay lens 23 is adjusted by changing the distance between the relay lens 23 and the streak tube 31 or by moving the stage 1.

The optical system from the objective lens 15 to the photocathode 32 and the optical system of the lighting device are housed in a light shield 25. The light shield 25 shields these optical systems from stray light.

The streak tube 31 is disposed so that the photocathode 32 is located at the position of image formation of the relay lens 23. The streak tube 31 constituted by the photocathode 32, a mesh grid 33, a convergent electrode 34, a pair of deflection electrodes 35, a microchannel plate 37 and a phosphor screen 38. A sweep voltage from a sweep voltage generating circuit 36 is applied to a pair of deflection electrodes 35. In the thus arranged streak tube 31, the slit image formed on the photocathode 32 is converted into an electron image and then the electron image reached the polarizing electrode 35 via the mesh grid 33 and the convergent electrode 34. The electron image is swept from the upper to the lower by the sweep voltage applied to the pair of deflection electrodes 35. The thus swept electron image is electronically intensified with the microchannel plate 37 and then re-converted into an optical image on the phosphor screen 38.

A relay lens 41 and a high-sensitive television camera 43 are disposed after the streak tube 31. The television camera 43 is provided to pick up the image on the phosphor screen 38 of the streak camera 31 and followed by a camera controller 44. The camera controller 44 is connected to an image processor 45 which is connected to both a computer 47 and a monitor television 49. The image processor 45 makes processing of the image signal fed from the television camera 43 to thereby provide the computer 47 and the monitor television 49 with the results. The computer 47 stores the results of image processing. Further, the computer 47 provides the actuator 3 for driving the stage 1 with a drive signal, provides the laser oscillator 5 with a pulse interval, provides the delay circuit 53 with a delay time and provides the image processor 45 with a processing condition. The monitor television 49 displays the slit image fetched by the streak tube 31 at real time, as well as displays the data of light intensity, wavelength and the like. In the case where the slit image is displayed on the monitor television 49, the streak tube 31 is operated in a stationary mode in which the width of the slit is enlarged to intensify the specimen image optically. On the other hand, the aforementioned focus adjustment, measurement range adjustment and chromatic aberration adjustment are carried out in a focusing mode of the streak camera.

A photodiode 51 is disposed in front of the semiconductor laser oscillator 5. The photodiode 51 is connected to the sweep voltage generating circuit 36 through an amplifier 52 and a delay circuit 53. The sweep voltage generating circuit 36 is triggered in synchronism with the laser pulse light.

FIG. 4 shows a second embodiment of the present invention, in which the same devices and parts as those shown in FIG. 3 are correspondingly referenced and therefore description about them is eliminated. FIG. 4 mainly illustrates a lighting device and an objective lens, and does not illustrate the other parts such as a relay lens 23, a streak tube 31 and the like.

In this embodiment, a slit 57 is provided adjacent to the stage 1. In addition to the downward illumination type, a transillumination type constituted by a beam splitter 61 and a reflecting mirror 62 is employed as the lighting device. An objective lens 65 is magnifying tandem lens. In this embodiment, the magnifying power up to about 10 can be attained.

Figure 5:
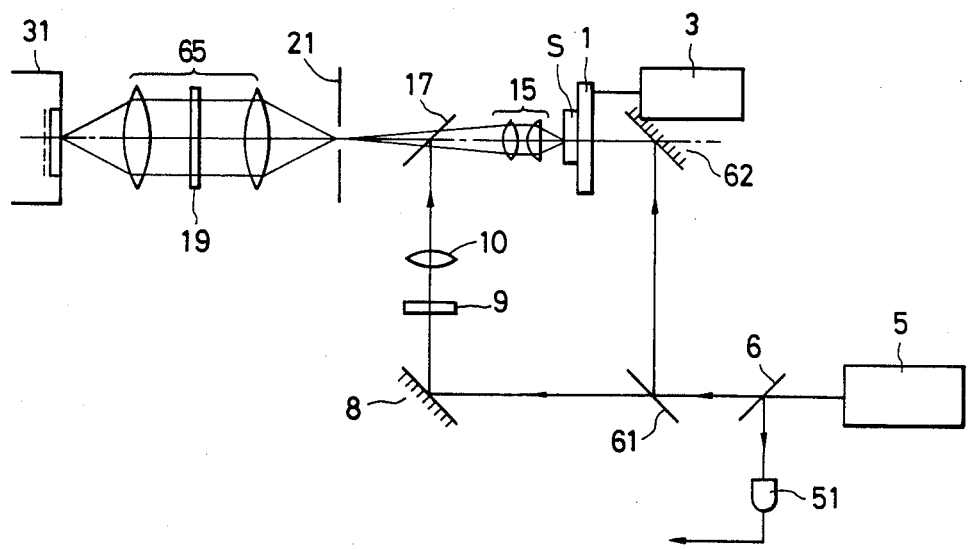

FIG. 5 shows a third embodiment of the present invention.

In this embodiment, a downward illumination type and a transillumination type are used in combination as the lighting device. The microscopic objective lens 15 of the first embodiment and the magnifying tandem lens 65 of the second embodiment are used in combination as a magnifying optical system. In this embodiment, the magnifying power up to 100 can be easily attained as the whole system.

Figure 6:
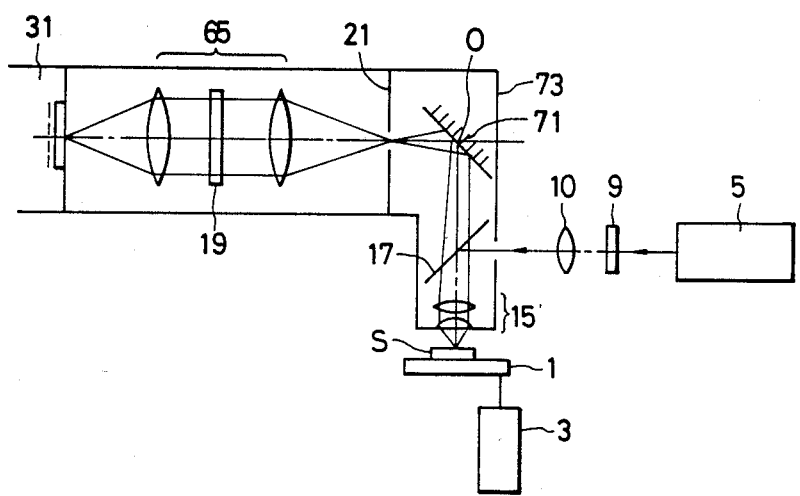

FIG. 6 shows a fourth embodiment of the present invention.

In this embodiment, the objective lens 15 is disposed so that the optical axis of the objective lens 15 can intersect the optical axis of the magnifying tandem lens 65 ( or the optical axis of the streak tube 31) at a desired angle. Further, a reflecting mirror 71 is disposed at the intersection point 0 of the two optical axes so as to be rotatable round an axis perpendicular to the two optical axes. The slit 21 is located between the reflecting mirror 71 and the tandem lens 65. The portion 73 of the light shield where the objective lens 15 is housed, is provided in the form of bellows so as to be flexible. The objective lens 15, together with the reflecting mirror 71, rotates round the axis perpendicular to the optical axis of the tandem lens 65. Thus, the specimen S can be observed from a desired angle.

In the following, an example of measurement by using the apparatus of embodiment 1 is described.

An objective lens 15 having 50 magnifying power was used, and a dye laser (400 nm) was used as a light source for irradiation. A band-pass interference filter was inserted into the optical system for irradiation so that only laser light of about 400 nm could be used as irradiating light for exciting a specimen. The irradiating light is applied to a cell incorporating hematoporphyrin to measure only fluorescent light of about 600 nm generated as that result. A band-pass interference filter for passing the aforementioned band was inserted into the image-forming optical system. Consequently, the HpD fluorescent intensity distribution and the fluorescence change with the passage of time at a desired point within the cell could be measured with high resolution. In the measurement, the spatial resolution was 1 $\mu$m and the time resolution was 10 ps.

It is to be understood that the present invention is not limited to the specific embodiments and that the filters 9 and 19 may be respectively replaced by density filter, interference filters, polarizing filters or color filters. Further, the image formed on the streak tube 31 may be recorded by a still camera.

Further, a short-pulse continuous light source may be used as the light source 5 for measurement with changing the pulse interval. In this case, the spatial change and optical change in a fine area of the specimen S for a short time (pulse interval) can be imaged. In addition, polarizing filters may be respectively inserted into the illumination optical system and the imaging optical system. In this case, the birefrengence change of the specimen S with the passage of time can be observed.

As described above, according to the present invention, the optical change of the specimen can be measured with the time resolution of the order of ps and the spatial resolution of the order of $\mu$ m. Further, the apparatus of the invention can be formed by combining a simple magnifying optical system with a streak camera, so that the apparatus is simple in construction and easy to handle.

What is claimed is:

1. A high spatial and time resolution measuring apparatus for optically measuring a desired area in a specimen, said apparatus comprising:
   a stage for mounting the specimen thereon;
   a light source for generating a first light;
   first optical means for directing said first light from said light source to said specimen;
   objective means for forming an image of second light emanating form said specimen;
   a width variable slit located at the image plane of said objective means for limiting the visual field of the specimen;
   relay lens means for forming an image of light emanating from said width variable slit at an image plane;
   a streak tube including a photocathode at the image plane of said relay lens means, said streak tube forming a streak image of an image formed by said relay lens means on said photocathode; and
   a housing for shielding said first optical means, said objective means, said width variable slit, and said relay lens from ambient light.

2. A high spatial and time resolution measuring apparatus for optically measuring a desired area in a specimen, said apparatus comprising:
   a stage disposed along an optical axis for mounting the specimen thereon, said stage being inclined relative to the optical axis to prevent light reflected by said stage from propagating along said optical axis;

a light source for generating a first light;

first optical means for directing said first light from said light source along an optical axis to said specimen;

objective means for forming an image of second light emanating from said specimen along said optical axis;

a width variable slit disposed at the image plane of said objective means along said optical axis for limiting the visual field of the specimen;

relay lens means disposed along said optical axis for forming an image of light emanating from said width variable slit at an image plane;

a streak tube including a photocathode disposed along said optical axis at the image plane of said relay lens means, said streak tube forming a streak image of an image formed by said relay lens means on said photocathode; and a housing for shielding said first optical means, said objective means, said width variable slit, and said relay lens from ambient light.

3. A high spatial and time resolution measuring apparatus according to claim 1 or 2, wherein said stage is slightly movable in the direction of an optical axis of said objective means and in the direction perpendicular to said optical axis.

4. A high spatial and time resolution measuring apparatus according to claim 1 or 2, wherein said first light is incident on said specimen from the side opposite to said stage with respect to said specimen.

5. A high spatial and time resolution measuring apparatus according to claim 1 or 2, wherein said first light is incident on said specimen through said stage.

6. A high spatial and time resolution measuring apparatus according to claim 1 or 2, wherein said first light is incident on said specimen both from the side opposite to said stage with said specimen and through said stage.

7. A high spatial and time resolution measuring apparatus according to claim 1 or 2, wherein said light source comprises a laser.

8. A high spatial and time resolution measuring apparatus according to claim 1 or 2, wherein said light source comprises a pulse light source.

9. A high spatial and time resolution measuring apparatus according to claim 1 or 2, wherein said light source comprises a short-pulse-continued light source variable in pulse interval.

10. A high spatial and time resolution measuring apparatus according to claim 1 or 2, wherein said first optical means includes a filter.

11. A high spatial and time resolution measuring apparatus according to claim 1 or 2, wherein said objective means comprises a microscopic objective lens.

12. A high spatial and time resolution measuring apparatus according to claim 1 or 2, wherein said objective means comprises a still camera lens.

13. A high spatial and time resolution measuring apparatus according to claim 1 or 2, wherein said objective means comprises a microscopic objective lens and a still camera lens arranged tandem.

14. A high spatial and time resolution measuring apparatus according to claim 1, wherein said relay lens means includes a filter.

15. A high spatial and time resolution measuring apparatus according to claim 1 or 2, said apparatus further comprising a reflecting mirror, wherein said objective means is disposed so that the optical axis of said objective means intersects the optical axis of said streak tube at a desired angle, and wherein said reflecting mirror is disposed at a point of intersection and is rotatable round an axis perpendicular to said two optical axes of said objective means and said streak tube.

16. A high spatial and time resolution measuring apparatus according to claim 1 or 2, wherein said first light is excitation light for said specimen and said second light is fluorescent light.

17. A high spatial and time resolution measuring apparatus according to claim 1 or 2, wherein said streak tube is used in a focusing mode to make one of slit width and a slit image width variable to thereby adjust said objective means.

18. A high spatial and time resolution measuring apparatus according to claim 1 or 2, said apparatus further comprising a television camera for picking up said streak image or a phosphor screen of said streak tube, and a controller for controlling drive of said stage, light emission of said light source, a deflection voltage of said streak tube, and said television camera.

19. A high spatial and time resolution measuring apparatus according to claim 18, wherein said streak tube is used in a focusing mode to make one of a slit width and slit image width variable to thereby adjust said objective means.

20. An apparatus as recited in claim 2, wherein said first optical means includes a first filter disposed along said optical axis, said first filter being inclined relative to the optical axis to prevent light reflected by said filter from propagating along said optical axis.

21. An apparatus as recited in claim 2, wherein said relay lens means includes a second filter disposed along said optical axis, said second filter being inclined relative to the optical axis to prevent light reflected by said second filter from propagating along said optical axis.

22. A high spatial and time resolution measuring apparatus according to claim 10, wherein said filter comprises a density filter.

23. A high spatial and time resolution measuring apparatus according to claim 10, wherein said filter comprises an interference filter.

24. A high spatial and time resolution measuring apparatus according to claim 10, wherein said filter comprises a polarizing filter.

25. A high spatial and time resolution measuring apparatus according to claim 14, wherein said filter comprises a density filter.

26. A high spatial and time resolution measuring apparatus according to claim 14, wherein said filter comprises an interference filter.

27. A high spatial and time resolution measuring apparatus according to claim 14, wherein said filter comprises a polarizing filter.

* * * * *